US007255736B2

(12) United States Patent
Pfaff et al.

(10) Patent No.: US 7,255,736 B2
(45) Date of Patent: Aug. 14, 2007

(54) EFFECT PIGMENTS BASED ON THIN $SiO_2$ FLAKES

(75) Inventors: Gerhard Pfaff, Muenster (DE); Doreen Warthe, Griesheim (DE); Johann Dietz, Dietzenbach (DE); Cornelia Foerderer, Heppenheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 11/246,564

(22) Filed: Oct. 11, 2005

(65) Prior Publication Data

US 2006/0112859 A1 Jun. 1, 2006

(30) Foreign Application Priority Data

Oct. 8, 2004 (DE) .................. 10 2004 049203

(51) Int. Cl.
C09C 3/06 (2006.01)
C09C 1/24 (2006.01)
C09C 1/28 (2006.01)
C09C 1/36 (2006.01)
A61K 8/25 (2006.01)
C04B 14/04 (2006.01)
C09D 11/00 (2006.01)
C08K 9/02 (2006.01)
A23L 1/27 (2006.01)

(52) U.S. Cl. ............... 106/482; 106/31.9; 106/439; 106/446; 106/457; 106/481; 47/57.6; 424/63; 426/250; 427/218; 428/408; 524/493

(58) Field of Classification Search ............... 106/403, 106/445, 446, 481, 482, 31.9, 439, 457; 47/57.6; 424/63; 426/250; 427/218; 428/404; 524/493
See application file for complete search history.

(56) References Cited

U.S. PATENT DOCUMENTS

| 4,971,697 | A | * | 11/1990 | Douden et al. ........... 210/502.1 |
|---|---|---|---|---|
| 5,104,632 | A | * | 4/1992 | Douden et al. ............ 423/335 |
| 5,753,024 | A | * | 5/1998 | Vogt et al. .................. 106/417 |
| 6,340,723 | B1 | * | 1/2002 | Nitta et al. ................. 524/430 |
| 6,511,536 | B1 | * | 1/2003 | Noguchi et al. ............ 106/417 |
| 6,602,934 | B1 | * | 8/2003 | Saito .......................... 523/216 |
| 6,630,018 | B2 | | 10/2003 | Bauer et al. |
| 6,656,259 | B2 | * | 12/2003 | Pfaff et al. .................. 106/415 |
| 6,997,982 | B2 | * | 2/2006 | Pfaff et al. .................. 106/415 |
| 2006/0042507 | A1 | * | 3/2006 | Bujard et al. ............... 106/415 |

FOREIGN PATENT DOCUMENTS

| JP | 07228515 A | * | 8/1995 |
|---|---|---|---|
| JP | 09-71417 A | * | 3/1997 |
| WO | WO93/08237 | | 4/1993 |

OTHER PUBLICATIONS

Machine Assisted Translation for JP7-228515-A (Aug. 29, 1995).*
Machine Assisted Translation for JP0-71417-A (Mar. 18, 1997).*

* cited by examiner

*Primary Examiner*—Anthony J. Green
(74) *Attorney, Agent, or Firm*—Millen, White, Zelano & Branigan, P.C.

(57) ABSTRACT

Effect pigments having improved optical properties based on $SiO_2$ flakes coated with one or more layers, where the $SiO_2$ flakes have a thickness of from 50 nm to 150 nm; processes for the preparation thereof; and use of these pigments in cosmetics, paints, coatings, plastics, films, in security printing, in security features in documents and identity cards, for coloring seed, for coloring foods or in medicament coatings and for the preparation of pigment compositions and dry preparations; are disclosed.

12 Claims, No Drawings

EFFECT PIGMENTS BASED ON THIN SiO$_2$ FLAKES

The present invention relates to effect pigments having improved optical properties based on SiO$_2$ flakes coated with one or more layers, where the SiO$_2$ flakes have a thickness of from 50 nm to 150 nm, to processes for the preparation thereof, and to the use of these pigments in cosmetics, paints, coatings, plastics, films, in security printing, in security features in documents and identity cards, for coloring seed, for coloring foods or in medicament coatings and for the preparation of pigment compositions and dry preparations.

The use of luster or effect pigments is widespread. Pigments of this type have become indispensable in automobile paints, decorative coatings of all types and in the coloring of plastics, in paints and printing inks, in particular inks for security printing, and in applications in decorative cosmetics. In the matrix surrounding them, these pigments ideally align parallel to the surface of the coating and exhibit their optical action through a complex interplay of interference, reflection and absorption of the incident light. A bright color, change between different colors depending on the viewing angle, so-called color flops, or changing brightness impressions are the focus of interest for the various applications.

Pigments of this type are generally prepared by coating flake-form metallic or non-metallic substrates with metal-oxide or metal layers. Most of these pigments are based on flake-form substrates comprising metals or natural phyllosilicates, such as mica, talc or glass.

The phyllosilicates, in particular, have the disadvantage that the thickness of the substrate varies in a broad range and cannot be set specifically, which results, even in the case of transparent substrates, in light transmission and reflection at the substrate occurring in a substantially uncontrollable manner and therefore not being utilizable in a targeted manner.

WO 93/08237 discloses effect pigments based on SiO$_2$ flakes which can be produced with reduced layer thickness variance by means of a belt technology. The thickness of the SiO$_2$ flakes described therein is usually between 200 nm and 2 μm, in particular 500 nm.

The pigments known to date do not enable all desired effects to be achieved, so that there is a constant demand for novel pigments which can be employed universally in a very wide variety of applications and exhibit novel and interesting color effects.

The above-mentioned demand is achieved by pigments in accordance with the present invention. The present invention accordingly relates to effect pigments having improved optical properties based on SiO$_2$ flakes coated with one or more layers, where the SiO$_2$ flakes have a thickness of from 50 nm to 150 nm.

The present invention likewise relates to processes for the preparation of these pigments, in which SiO$_2$ flakes having a thickness of from 50 nm to 150 nm are coated with one or more layers.

The pigments according to the invention have the advantage that they can be employed universally in a very wide variety of applications. The effect pigments exhibit novel effects which were not achievable using the pigments from the prior art or were not expected in this form. The basis for these unexpected effects is the combination of a plurality of properties of the effect pigments according to the invention. Firstly, the effect pigments have a very thin substrate having a thickness in the range from 50 to 150 nm which influences the optical properties of the effect pigments in a particular manner. Secondly, the substrate is a synthetic SiO$_2$ flake which is distinguished by high transparency and a uniform layer thickness. The combination of these particular features results in surprising and unique effects in corresponding effect pigments and thus opens up access to novel pigments having particular properties.

Owing to the advantageous properties, the effect pigments according to the invention are universally suitable for a large number of varied applications. The present invention accordingly also relates to the use of these pigments in cosmetics, paints, coatings, plastics, films, in security printing, in security features in documents and identity cards, for coloring seed, for coloring foods or in medicament coatings and for the preparation of pigment compositions and dry preparations.

The pigments according to the invention are based on flake-form silicon di-oxide particles which have a uniform layer thickness and are preferably prepared in accordance with the international application WO 93/08237 on a continuous belt by solidification and hydrolysis of a water-glass solution. The term "uniform layer thickness" here is taken to mean a layer-thickness tolerance of from 3 to 10%, preferably from 3 to 5%, of the total dry-layer thickness of the particles. The flake-form silicon dioxide particles are generally in amorphous form. Synthetic flakes of this type have the advantage over natural materials, such as, for example, mica, that the layer thickness can be set with regard to the desired effects and the layer-thickness tolerance is limited.

The diameter of the substrates is preferably between 1 and 250 μm, more preferably between 2 and 100 μm. Their thickness is between 50 and 150 nm. The mean aspect ratio of the flake-form substrates, i.e. the ratio of the mean length measurement value, which corresponds to the mean diameter here, to the mean thickness measurement value, is preferably from 5 to 200, more preferably from 20 to 150 and particularly preferably from 30 to 120.

The said substrates are coated with one or more layers in the pigments according to the invention; the SiO$_2$ flakes are preferably coated with one layer.

The one or more layers here comprise metal oxides, metal oxide hydrates, metal suboxides, metals, metal fluorides, metal nitrides, metal oxynitrides and/or mixtures of these materials. The metal oxide, metal oxide hydrate, metal suboxide, metal, metal fluoride, metal nitride, metal oxynitride layers and/or the mixtures thereof can be of low refractive index (refractive index <1.8) or of high refractive index (refractive index ≧1.8). Suitable metal oxides and metal oxide hydrates are all metal oxides or metal oxide hydrates known to the person skilled in the art, such as, for example, aluminum oxide, aluminum oxide hydrate, silicon oxide, silicon oxide hydrate, iron oxide, tin oxide, cerium oxide, zinc oxide, zirconium oxide, chromium oxide, titanium oxide, in particular titanium dioxide, titanium oxide hydrate and mixtures thereof, such as, for example, ilmenite or pseudobrookite. Metal suboxides which can be employed are, for example, the titanium suboxides. Suitable metals are, for example, chromium, aluminum, nickel, silver, gold, platinum, lead, germanium, titanium, copper or alloys, and a suitable metal fluoride is, for example, magnesium fluoride. Metal nitrides or metal oxynitrides which can be employed are, for example, the nitrides or oxynitrides of the metals titanium, zirconium and/or tantalum. Preferably metal oxide, metal, metal fluoride and/or metal oxide hydrate layers and very particularly preferably metal oxide and/or metal oxide hydrate layers are applied to the SiO$_2$ flakes. Furthermore, multilayered structures comprising high- and low-refractive-index metal oxide, metal oxide hydrate, metal or metal fluoride layers may also be present, with high- and low-refractive-index layers preferably alternating. Particular preference is given to layer packages comprising a high-refractive-index layer and a low-refractive-index layer, where one or more of these layer packages may be applied to the SiO$_2$ flakes. In a further embodiment, colorants may be added to the metal oxide, metal oxide hydrate, metal suboxide, metal, metal fluoride, metal nitride or metal oxynitride layers or mixtures thereof. Suitable colorants are, for example, organic or inorganic colored pigments, such as colored metal oxides, for example magnetite, chromium oxide, or colored pigments, such as, for example, Berlin Blue, ultramarine, bismuth vanadate, Thénard's Blue, or alternatively organic colored pigments, such as, for example, indigo, azo pigments, phthalocyanines or also Carmine Red.

In a preferred embodiment, only one layer is applied to the SiO$_2$ flakes. This one layer preferably comprises one or more metal oxides, in particular titanium dioxide and/or iron oxide.

The thickness of the one or more layers is from 20 to 500 nm and is ideally matched to the desired effect or to the thickness of the SiO$_2$ flakes. Thus, in the case of coating of the SiO$_2$ flakes with a layer of titanium dioxide, silver-white effect pigments are obtained. The layer thickness of the SiO$_2$ flakes here is from 50 to 150 nm, preferably from 50 to 120 nm and very particularly preferably from 50 to 100 nm. The thickness of the titanium oxide layer is preferably in the range from 20 to 200 nm, in particular in the range from 30 to 180 nm and very particularly preferably in the range from 40 to 150 nm. Silver-white effect pigments can only be achieved through the use of the thin SiO$_2$ flakes since, in the case of greater substrate thicknesses, the inherent interference of the substrate flakes which then occurs prevents the occurrence of the silver-white effect. The silver-white effect pigments according to the invention are distinguished by a particularly pure silver-white effect and higher luster, which cannot be achieved in this way with pigments based on natural mica.

If SiO$_2$ flakes having a layer thickness of from 120 to 150 nm are coated with one or more layers comprising titanium dioxide or iron oxide, colored interference pigments are obtained. The layer thickness of the one or more layers here is usually from 50 to 500 nm, preferably from 50 to 400 nm and in particular from 50 to 250 nm. The colored interference pigments have clearer interference colors than conventional interference pigments, with the interference colors exhibiting virtually no angle dependence. In the case of pigments from the prior art having thicker SiO$_2$ substrates, by contrast, angle-dependent color effects are frequently observed, which are not always desired in a number of applications and color creations.

In addition, the effect pigments according to the invention are also suitable for the provision of effect pigments having a non-flake appearance. The non-flake appearance is an effect which can be observed on use of the pigments in the application medium, for example a surface coating. On occurrence of this effect, the eye is no longer able to resolve the individual pigment particles aligned in parallel in the application medium, i.e. the individual particles are no longer perceived by the eye. This is particularly desirable in applications where the most homogeneous overall impression possible is to be conveyed, such as, for example, in automobile or industrial paints. This effect is very difficult, but in most cases impossible, to achieve using pigments from the prior art. Thus, although, for example, BiOCl is suitable for generating this effect, it is only used rarely owing to the instability to light. The effect pigments according to the invention thus allow the provision of pigments having a non-flake appearance at the same time as ensuring adequate stability of the pigments to light and chemical influences. Effect pigments according to the invention having a non-flake appearance are based on SiO$_2$ flakes having a layer thickness of from 50 to 100 nm which are coated with one or more layers, preferably with a layer of a metal oxide, in particular of titanium dioxide and/or iron oxide, being present. The layer thickness here is from 50 to 500 nm, preferably from 20 to 200 nm.

Effect pigments having different colorings and effects which can only be achieved with difficulty or not at all by other methods can thus be produced on the basis of thin SiO$_2$ flakes.

In a further embodiment of the present invention, the effect pigments according to the invention may furthermore be provided with an additional stabilizing organic and/or inorganic coating as outer layer. Examples of coatings of this type are given, for example, in EP 0 632 109, U.S. Pat. No. 5,759,255, DE 43 17 019, DE 39 29 423, DE 32 35 017, EP 0 492 223, EP 0 342 533, EP 0 268 918, EP 0 141 174, EP 0 764 191, WO 98/13426 or EP 0 465 805, the disclosures of which are hereby incorporated herein by reference. Besides the improved optical properties already mentioned, effect pigments having an organic coating, for example of organosilanes or organotitanates or organozirconates, additionally exhibit increased stability to weathering influences, such as, for example, moisture and light, which is of particular interest, above all, for industrial coatings and in the automobile sector. The stabilization can be improved by inorganic components of the additional coating. Overall, the respective contents for the additional stabilising coating should be selected so that the optical properties of the effect pigments according to the invention are not significantly affected.

Suitable organosilanes for the additional stabilizing coating are, for example, silanes of the general formula

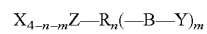

$$X_{4-n-m}Z-R_n(-B-Y)_m$$

where X=OH, halogen, alkoxy, aryloxy

Z=Si

R=alkyl, phenyl or hydrogen

B=organic, at least bifunctional group (alkylene, alkyleneoxyalkylene)

Y=alkyl, amino, substituted amino, hydroxyl, hydroxyalkyl, siloxane, acetoxy, isocyanate, vinyl, acryloyl, epoxy, epoxypropoxy, imidazole or ureido group n, m=0, 1, 2, 3, where n+m≦3.

The organosilanes consist of an anchor group ($X_{4-n-m}Z$), which is able to bind, for example, to the surface of the pigment, at least one hydrophobic group (R,B) and one or more alkyl or functional groups (Y). The anchor group preferably consists of alkoxysilanes, which can be converted into corresponding hydroxyl groups by hydrolytic reaction conditions.

The organosilane can be matched to requirements through the choice of suitable functional groups. In addition, depending on the coating sequence, additional bonds can be formed between pigment and medium via the organosilane through reaction of the functional groups with corresponding functionalities in the application media. In a particular embodiment, the surface of the effect pigments according to the invention is modified by means of a combination of organic functionalities matched to the use medium. Also suitable for this purpose is the use of mixtures of various organosilanes.

The hydrophobicity of the particle surface can likewise be matched by integration of alkyl-containing coupling reagents, such as, for example, alkylsilanes. Besides the organosilanes, it is also preferred to use hydrolysates thereof and homogeneous and heterogeneous oligomers and/or polymers thereof, which can likewise be employed alone or in combination with the silanes already described. Particular preference is given to mixtures of various organosilanes, in particular with functional groups Y which are different from one another, the use of which guarantees a particularly wide range of applications.

Examples of organosilanes are propyltrimethoxysilane, propyltriethoxysilane, isobutyltrimethoxysilane, n-octyltrimethoxysilane, i-octyltrimethoxysilane, n-octyltriethoxysilane, n-decyltrimethoxysilane, dodecyltrimethoxysilane, hexadecyltrimethoxysilane, vinyltrimethoxysilane, octadecyltrimethoxysilane, preferably vinyltrimethoxysilane. Suitable oligomeric, alcohol-free organosilane hydrolysates are, inter alia, the products marketed under the trade name "Dynasylan®" by Sivento, such as, for example, Dynasylan HS 2926, Dynasylan HS 2909, Dynasylan HS2907, Dynasylan HS 2781, Dynasylan HS 2776, Dynasylan HS 2627. Also suitable as organic coatings are oligomeric vinylsilane and aminosilane hydrolysate. Functionalized organosilanes are, for example, 3-aminopropyltrimethoxysilane, 3-methacryloxytrimethoxysilane, 3-glycidyloxypropyltrimethoxysilane, beta-(3,4-epoxycyclohexyl)ethyltrimethoxysilane, gamma-isocyanatopropyltrimethoxysilane, 1,3-bis(3-glycidoxypropyl)-1,1,3,3-tetramethyldisiloxane, ureidopropyltriethoxysilane, preferably 3-aminopropyltrimethoxysilane, 3-methacryloxytrimethoxysilane, 3-glycidyloxypropyltrimethoxysilane, beta-(3,4-epoxycyclohexyl)ethyltrimethoxysilane, gamma-isocyanatopropyltrimethoxysilane. Examples of polymeric silane systems are described in WO 98/13426 and are marketed, for example, by Sivento under the trade name Hydrosil®.

The present invention likewise relates to processes for the preparation of the effect pigments according to the invention in which $SiO_2$ flakes having a thickness of from 50 nm to 150 nm are coated with one or more layers. Suitable materials for the one or more layers have already been mentioned above.

The coating with one or more layers can be carried out by wet-chemical methods, by sol-gel processes and/or by CVD or PVD processes.

The processes according to the invention for the preparation of the effect pigments are preferably wet-chemical processes, in which the known wet-chemical coating technologies developed for the preparation of pearlescent pigments can be used and which are described, for example, in the following publications: DE 14 67 468, DE 19 59 988, DE 20 09 566, DE 22 14 545, DE 22 15 191, DE 22 44 298, DE 23 13 331, DE 25 22 572, DE 31 37 808, DE 31 37 809, DE 31 51 343, DE 31 51 354, DE 31 51 355, DE 32 11 602, DE 32 35 017.

For the coating, the flake-form substrate is suspended in water and coated one or more times with a metal oxide, metal oxide hydrate, metal suboxide, metal, metal fluoride, metal nitride, metal oxynitride and/or mixtures thereof by addition and precipitation of the corresponding inorganic metal compounds, during which the pH necessary for precipitation of the respective metal oxide, metal oxide hydrate, metal suboxide, metal, metal fluoride, metal nitride or metal oxynitride is set and kept constant by simultaneous addition of acid or base, and the coated substrate is subsequently separated off from the aqueous suspension, dried and optionally calcined.

The calcination temperature here can be optimized with respect to the coating present in each case. Preferably, however, the calcination temperature is between 250 and 1000° C., in particular between 350 and 900° C. In the case of application of a plurality of layers, the pigments can be separated off, dried and optionally calcined after application of each individual layer, before being re-dispersed for application of the next layer.

If the layer comprises $TiO_2$, the process described in U.S. Pat. No. 3,553,001 is preferably employed for application of these layers. In this process, an aqueous solution of an inorganic titanium salt is slowly added to a suspension, heated to about 50-100° C., in particular 70-80° C., of the flake-form, optionally already pre-coated substrates, and the pH is kept substantially constant at from 0.5 to 5, in particular from about 1.5 to 2.5, by simultaneous metered addition of a base. As soon as the desired layer thickness of the $TiO_2$ oxide hydrate has been reached, the addition of the titanium salt solution and the base is terminated. This process is also known as the titration process and has the special feature that there is no excess of titanium salt, but instead only an amount as is necessary for uniform coating with the hydrated $TiO_2$ and can also be accommodated by the surface of the substrate to be coated is always provided per time unit. The solution therefore contains no hydrated titanium dioxide particles, which are not deposited on the surface to be coated.

In principle, CVD or PVD processes are also suitable for the coating, in particular with metals, for the preparation of the pigments according to the invention. It is necessary here for the substrate to be kept uniformly in motion during the vapour-deposition process in order that homogeneous coating of all surfaces is ensured.

In addition, in a process which is likewise in accordance with one embodiment of the invention, a stabilizing organic and/or inorganic coating can additionally be applied as outer layer. Examples of coating processes of this type are given, inter alia, in EP 0 632 109, U.S. Pat. No. 5,759,255, DE 43 17 019, DE 39 29 423, DE 32 35 017, EP 0 492 223, EP 0 342 533, EP 0 268 918, EP 0 141 174, EP 0 764 191, WO 98/13426 or EP 0 465 805. Examples of organic coatings and the advantages associated therewith have already been described above under the structure of the pigments according to the invention. The process step of application of the organic coating can be carried out immediately after the other steps of the process according to the invention. The substances applied in this step preferably comprise a proportion by weight of from 0.1 to 5% by weight, more preferably from 0.5 to 3% by weight, more of the pigment as a whole.

The effect pigments according to the invention are versatile in application and can be employed in many areas. Accordingly, the present invention likewise relates to the use of the pigments according to the invention in cosmetics, paints, coatings, plastics, films, in security printing, in security features in documents and identity cards, for coloring seed, for coloring foods or in medicament coatings and for the preparation of pigment compositions and dry preparations.

In the case of cosmetics, the effect pigments according to the invention are particularly suitable for products and formulations of decorative cosmetics, such as, for example, nail varnishes, coloring powders, lipsticks or eye-shadows, soaps, toothpastes, etc. The effect pigments according to the invention can of course also be combined in the formulations with cosmetic raw materials and assistants of any type. These include, inter alia, oils, fats, waxes, film formers, preservatives and assistants which generally determine the applicational properties, such as, for example, thickeners and rheological additives, such as, for example, bentonites, hectorites, silicon dioxide, Ca silicates, gelatine, high-molecular-weight carbohydrates and/or surfaceactive assistants, etc. Formulations comprising the effect pigments according to the invention can be of the lipophilic, hydrophilic or hydrophobic type. In the case of heterogeneous formulations having discrete aqueous and non-aqueous phases, the particles according to the invention may in each case be present in only one of the two phases or distributed over both phases.

The pH values of the aqueous formulations can be between 1 and 14, preferably between 2 and 11 and particularly preferably between 5 and 8. The concentrations of the effect pigments according to the invention in the formulation are unlimited. They can be—depending on the application—between 0.001 (rinse-off products, for example shower gels) and 99% (for example luster-effect articles for particular applications). The effect pigments according to the invention may furthermore also be combined with cosmetic active ingredients. Suitable active ingredients are, for example, insect repellents, UV A/BC protection filters (for example OMC, B3, MBC), antiageing active ingredients, vitamins and derivatives thereof (for example vitamin A, C, E, etc.), self-tanning agents (for example DHA, erythrulose, inter alia) and further cosmetic active ingredients, such as, for example, bisabolol, IPO, ectoine, emblica, allantoin, bioflavonoids and derivatives thereof.

On use of the effect pigments in surface coatings and inks, all areas of application known to the person skilled in the art are possible, such as, for example, powder coatings, automobile paints, printing inks for gravure, off-set, screen or flexographic printing, and for coatings in outdoor applications. The surface coatings and inks here may, for example, be radiation-curing, physically drying or chemically curing. For the preparation of printing inks or liquid coatings, a multiplicity of binders, for example based on acrylates, methacrylates, polyesters, polyurethanes, nitrocellulose, ethylcellulose, polyamide, polyvinyl butyrate, phenolic resins, maleic resins, starch or polyvinyl alcohol, amine resins, alkyd resins, epoxy resins, polytetrafluoroethylene, polyvinylidene fluorides, polyvinyl chloride or mixtures thereof, is suitable, in particular water-soluble products. The surface coatings can be powder coatings or water- or solvent-based coatings, where the choice of coating constituents is subject to the general knowledge of the person skilled in the art. Common polymeric binders for powder coatings are, for example, polyesters, epoxides, polyurethanes, acrylates or mixtures thereof.

In addition, the effect pigments according to the invention can be used in films and plastics, for example in agricultural sheeting, infrared-reflective films and sheets, gift foils, plastic containers and moldings for all applications known to the person skilled in the art. Suitable plastics for incorporation of the effect pigments according to the invention are all common plastics, for example thermosets or thermoplastics. The possible applications and plastics, processing methods and additives which can be employed are described, for example, in RD 472005 or in R. Glausch, M. Kieser, R. Maisch, G. Pfaff, J. Weitzel, Perlglanzpigmente [Pearlescent Pigments], Curt R. Vincentz Verlag, 1996, 83 ff., the disclosure of which is incorporated herein by reference.

In addition, the effect pigments according to the invention are also suitable for use in security printing and in security-relevant features for, for example, counterfeiting-proof cards and identity cards, such as, for example, entry tickets, personal identity cards, banknotes, cheques and cheque cards, and for other counterfeiting-proof documents. In the area of agriculture, the effect pigments can be used for the coloring of seed and other starting materials, in addition in the foods sector for pigmenting foods. The effect pigments according to the invention can likewise be employed for pigmenting coatings in medicaments, such as, for example, tablets or dragees.

The effect pigments according to the invention are likewise suitable in the above-mentioned areas of application for use in blends with organic dyes and/or pigments, such as, for example, transparent and opaque, white, colored and black pigments, luminescent dyes and/or pigments and with flake-form iron oxides, organic pigments, holographic pigments, LCPs (liquid crystal polymers) and conventional transparent, colored and black luster pigments based on metal oxide-coated flakes based on mica, glass, $Al_2O_3$, $Fe_2O_3$, $SiO_2$, etc. The effect pigments according to the invention can be mixed in any ratio with commercially available pigments and fillers.

Fillers which may be mentioned are, for example, natural and synthetic mica, nylon powder, pure or filled melamine resins, talc, glasses, kaolin, oxides or hydroxides of aluminum, magnesium, calcium, zinc, BiOCl, barium sulfate, calcium sulfate, calcium carbonate, magnesium carbonate, carbon, and physical or chemical combinations of these substances. There are no restrictions regarding the particle shape of the filler. In accordance with requirements, it can be, for example, flake-form, spherical or needle-shaped.

The effect pigments according to the invention are furthermore suitable for the preparation of flowable pigment compositions and dry preparations comprising one or more particles according to the invention, binders and optionally one or more additives. The term "dry preparations" is also taken to mean preparations which comprise from 0 to 8% by weight, preferably from 2 to 8% by weight, in particular from 3 to 6% by weight, of water and/or a solvent or solvent mixture. The dry preparations are preferably in the form of pellets, granules, chips, sausages or briquettes and have particle sizes of preferably 0.2-80 mm. The dry preparations are used, in particular, in the preparation of printing inks and in cosmetic formulations.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

EXAMPLES

Example 1

100 g of $SiO_2$ flakes (125 nm thick, particle size 5-50 µm) are heated to 75° C. in 2 l of demineralized water. At a stirrer speed of 1300 rpm, 17 g of 50% $SnCl_4$ solution are added. During this addition, the pH is kept constant at pH 1.4 using potassium hydroxide solution (30% by weight). The pH is subsequently lowered to pH 1.3 using hydrochloric acid (10% by weight). At this pH, 600 g of $TiCl_4$ solution (400 g/l) are added. The pH of 1.3 is kept constant using potassium hydroxide solution (30%). After addition of the $TiCl_4$ solution, the pH is raised to pH 6 using potassium hydroxide solution (30%), and the mixture is stirred for a further 15 min. The product is filtered off and rinsed with demineralised water. After drying at 110° C., it is calcined at 800° C.

A silver-white effect pigment having high luster is obtained.

Example 2

100 g of $SiO_2$ flakes (125 nm thick, particle size 5-50 μm) are heated to 75° C. in 2 l of demineralized water. At a stirrer speed of 1300 rpm, 17 g of 50% $SnCl_4$ solution are added. During this addition, the pH is kept constant at pH 1.4 using potassium hydroxide solution (30% by weight). The pH is subsequently lowered to pH 1.3 using hydrochloric acid (10% by weight). At this pH, 1200 g of $TiCl_4$ solution (400 g/l) are added. The pH of 1.3 is kept constant using potassium hydroxide solution (30%). After addition of the $TiCl_4$ solution, the pH is raised to pH 6 using potassium hydroxide solution (30%), and the mixture is stirred for a further 15 min. The product is filtered off and rinsed with demineralised water. After drying at 110° C., it is calcined at 800° C.

An interference pigment having high luster and a blue interference color is obtained.

Example 3

100 g of $SiO_2$ flakes (80 nm thick, particle size 5-50 μm) are heated to 75° C. in 2 l of demineralized water. At a stirrer speed of 1300 rpm, 17 g of 50% $SnCl_4$ solution are added. During this addition, the pH is kept constant at pH 1.4 using potassium hydroxide solution (30% by weight). The pH is subsequently lowered to pH 1.3 using hydrochloric acid (10% by weight). At this pH, 1200 g of $TiCl_4$ solution (400 g/l) are added. The pH of 1.3 is kept constant using potassium hydroxide solution (30%). After addition of the $TiCl_4$ solution, the pH is raised to pH 6 using potassium hydroxide solution (30%), and the mixture is stirred for a further 15 min. The product is filtered off and rinsed with demineralised water. After drying at 110° C., it is calcined at 800° C.

An effect pigment which, after incorporation into an application medium, exhibits a non-flake appearance, i.e. the individual pigment particles cannot be resolved by the eye, is obtained.

The entire disclosure of all applications, patents and publications, cited herein and of corresponding German application No. 10 2004 049203.4, filed Oct. 8, 2004 is incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. An effect pigment which is a silver-white effect pigment, a colored interference pigment or an effect pigment having a non-flake appearance comprising an $SiO_2$ flake substrate having a thickness of from 50 nm to 150 nm, coated with only one layer of a metal oxide, metal oxide hydrate, metal suboxide, or metal fluoride or only one layer of a mixture of two or more of these materials.

2. An effect pigment according to claim 1, wherein the layer is a metal oxide layer of iron oxide and/or titanium dioxide.

3. An effect pigment according to claim 1, wherein the thickness of the layer is 20-500 nm.

4. An effect pigment according to claim 1, wherein the $SiO_2$ flake substrate is of synthetic $SiO_2$.

5. An effect pigment of claim 1, wherein the $SiO_2$ flake substrate has a uniform layer thickness such that the layer-thickness tolerance is from 3 to 10% of the total thickness of the substrate.

6. An effect pigment of claim 1, wherein the $SiO_2$ flake substrate has a layer thickness of 120 to 150 nm.

7. An effect pigment of claim 1, wherein the $SiO_2$ flake substrate has a layer thickness of 50 to 100 nm.

8. A process for preparing an effect pigment according to claim 1, which comprises coating an $SiO_2$ flake substrate having a thickness of from 50 nm to 150 nm with only one layer of a metal oxide, metal oxide hydrate, metal suboxide or metal fluoride or only one layer of a mixture of two or more of these materials.

9. A process according to claim 8, wherein the coating with only one layer is carried out by a wet-chemical method, a sol-gel process and/or a CVD or PVD process.

10. A cosmetic, paint or plastic composition, a coating or film, a security printing, document or identity card, an agricultural seed, a foodstuff or a medicament coating comprising a pigment according to claim 1.

11. A pigment composition comprising a pigment according to claim 1.

12. A pigment composition of claim 11, which is a dry preparation composition.

* * * * *